United States Patent [19]

Gambale

[11] Patent Number: 5,409,459
[45] Date of Patent: Apr. 25, 1995

[54] WINDOWED CATHETER AND METHOD OF USE

[75] Inventor: Richard A. Gambale, Tyngsboro, Mass.

[73] Assignee: C. R. Bard, Inc., Murray Hill, N.J.

[21] Appl. No.: 295,222

[22] Filed: Aug. 24, 1994

Related U.S. Application Data

[63] Continuation of Ser. No. 30,841, Mar. 12, 1993, abandoned.

[51] Int. Cl.⁶ .................. A61M 25/00; A61M 29/00
[52] U.S. Cl. ................................ 604/96; 604/102; 606/192
[58] Field of Search .................. 604/96–103, 604/49–53; 606/192–196; 600/18

[56] References Cited

U.S. PATENT DOCUMENTS

| | | | |
|---|---|---|---|
| 3,769,981 | 11/1973 | McWhorter | 604/96 |
| 4,552,554 | 11/1985 | Gould et al. | 604/51 |
| 4,643,712 | 2/1987 | Kulik et al. | 604/4 |
| 4,662,368 | 5/1987 | Hussein et al. | |
| 4,690,138 | 9/1987 | Heyden | 128/207.15 |
| 4,705,507 | 11/1987 | Boyles | 604/101 |
| 4,748,982 | 6/1988 | Horzewski et al. | |
| B1 4,762,129 | 7/1991 | Bonzel | 606/194 |
| 4,771,777 | 9/1988 | Horzewski et al. | |
| 4,813,930 | 3/1989 | Elliott | 604/53 |
| 4,824,435 | 4/1989 | Giesy et al. | 604/49 |
| 4,932,413 | 6/1990 | Shockey et al. | 128/657 |
| 4,943,278 | 7/1990 | Euteneuer et al. | 604/96 |
| 4,944,745 | 7/1990 | Sogard et al. | 606/194 |
| 4,947,864 | 8/1990 | Shockey et al. | 128/772 |
| 4,988,356 | 1/1991 | Crittenden et al. | 606/192 |
| 5,040,548 | 8/1991 | Yock | 128/898 |
| 5,046,503 | 9/1991 | Schneiderman | 128/692 |
| 5,061,273 | 10/1991 | Yock | 606/194 |
| 5,135,535 | 8/1992 | Kramer | 606/194 |
| 5,154,725 | 10/1992 | Leopold | 606/194 |
| 5,171,222 | 12/1992 | Euteneuer et al. | 604/102 |
| 5,195,978 | 3/1993 | Schiffer | 604/161 |
| 5,205,822 | 4/1993 | Johnson et al. | 604/96 |
| 5,263,932 | 11/1993 | Jang | 604/96 |

FOREIGN PATENT DOCUMENTS

| | | |
|---|---|---|
| 0380873 | 8/1990 | European Pat. Off. |
| 0441384 | 8/1991 | European Pat. Off. |
| 627828 | 10/1978 | U.S.S.R. |

OTHER PUBLICATIONS

Bjorn Nordenstrom, "New Instruments for Catheterization and Angiocardiography", *Radiology*, V85, 1965.
Bjorn Nordenstrom, "Balloon Catheters for Percutaneous Insertion into the Vascular System", Department of Diagnostic Roentgenology, 1962.

*Primary Examiner*—John D. Yasko
*Assistant Examiner*—Adam J. Cermak
*Attorney, Agent, or Firm*—Morgan & Finnegan

[57] ABSTRACT

An over-the-wire catheter includes an elongated shaft having a guidewire lumen extending substantially the entire length of the catheter for receiving a guidewire. The catheter has a length relative to the guidewire such that the guidewire can simultaneously extend out the proximal and distal ends of the catheter. The catheter shaft includes a window opening the guidewire lumen to the exterior of the catheter. The window is of such a length and is so located on the shaft that as the catheter is withdrawn proximally over the guidewire, the window is exposed to provide access to the guidewire before the proximal end of the guidewire is disposed distal to the proximal end of the catheter and such that the distal end of the catheter is exposed to provide access to the guidewire extending therefrom before the proximal end of the guidewire is disposed distal to the window.

10 Claims, 4 Drawing Sheets

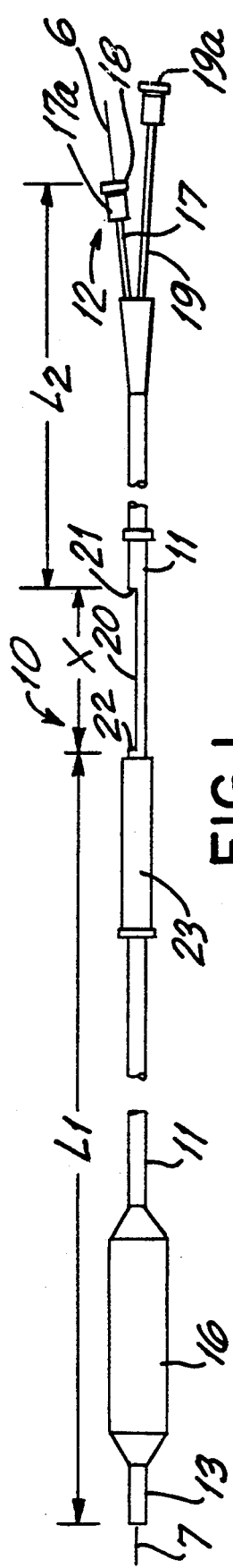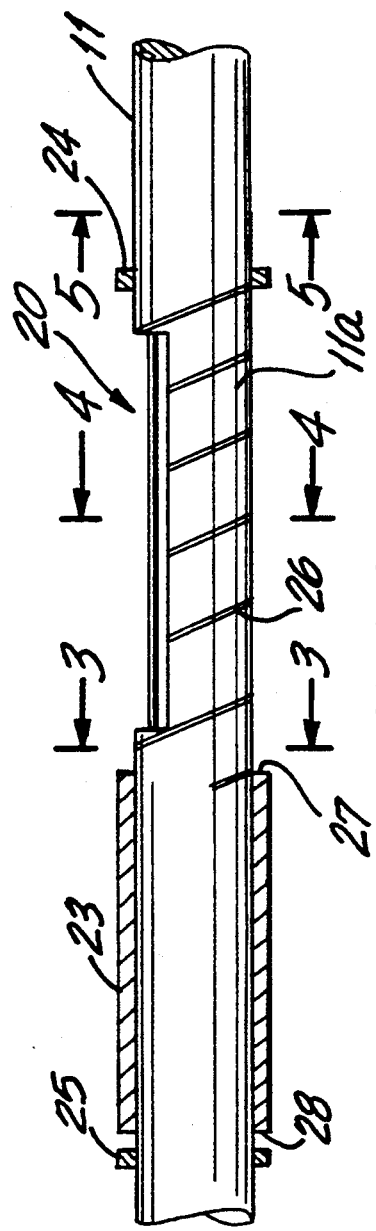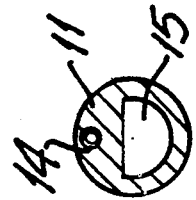

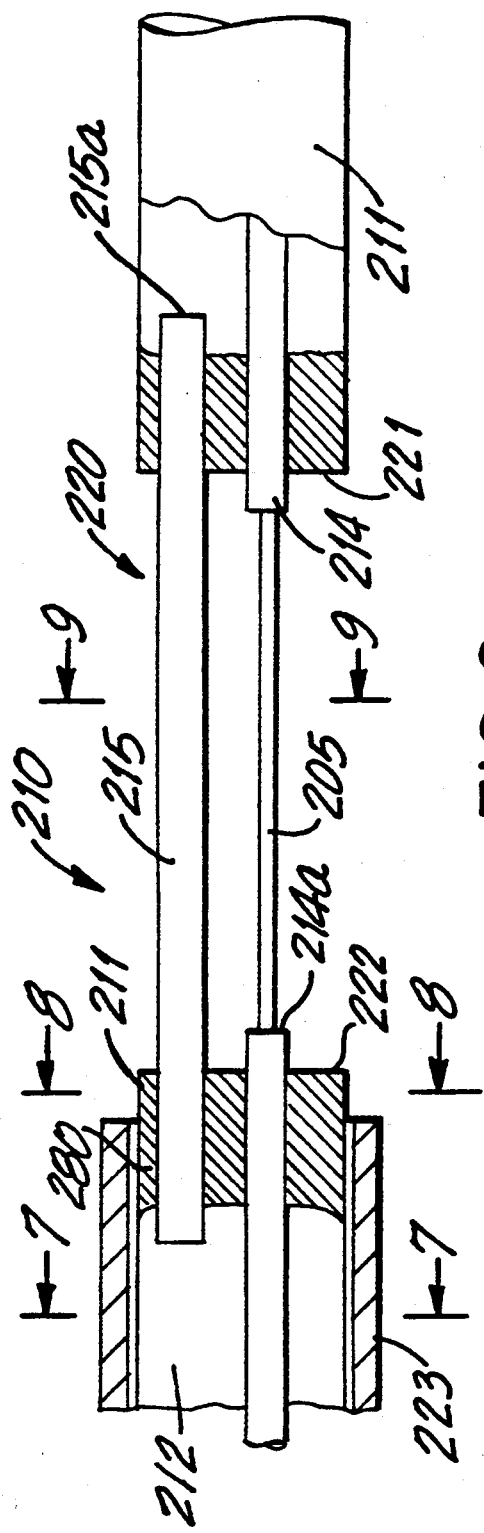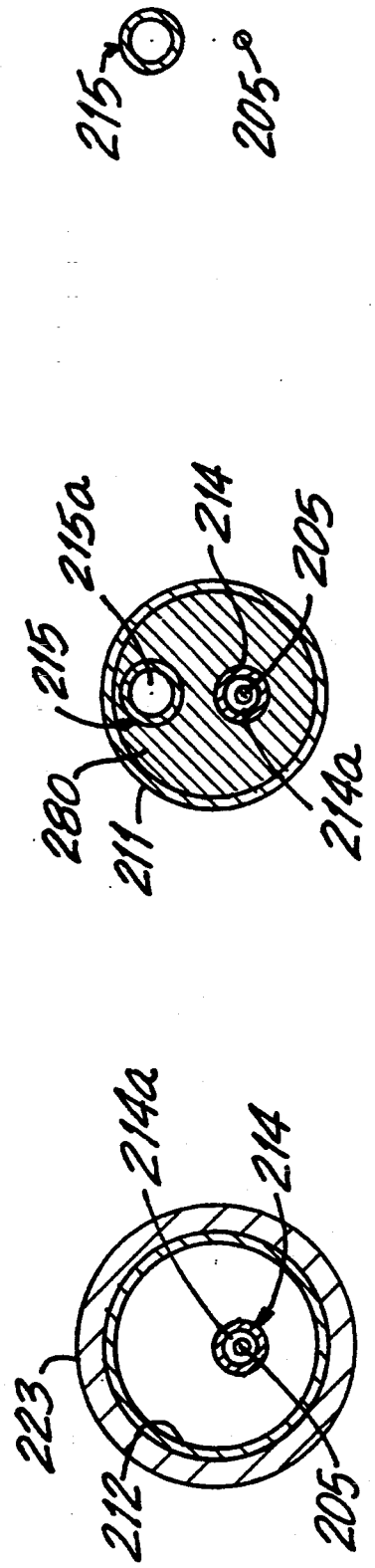

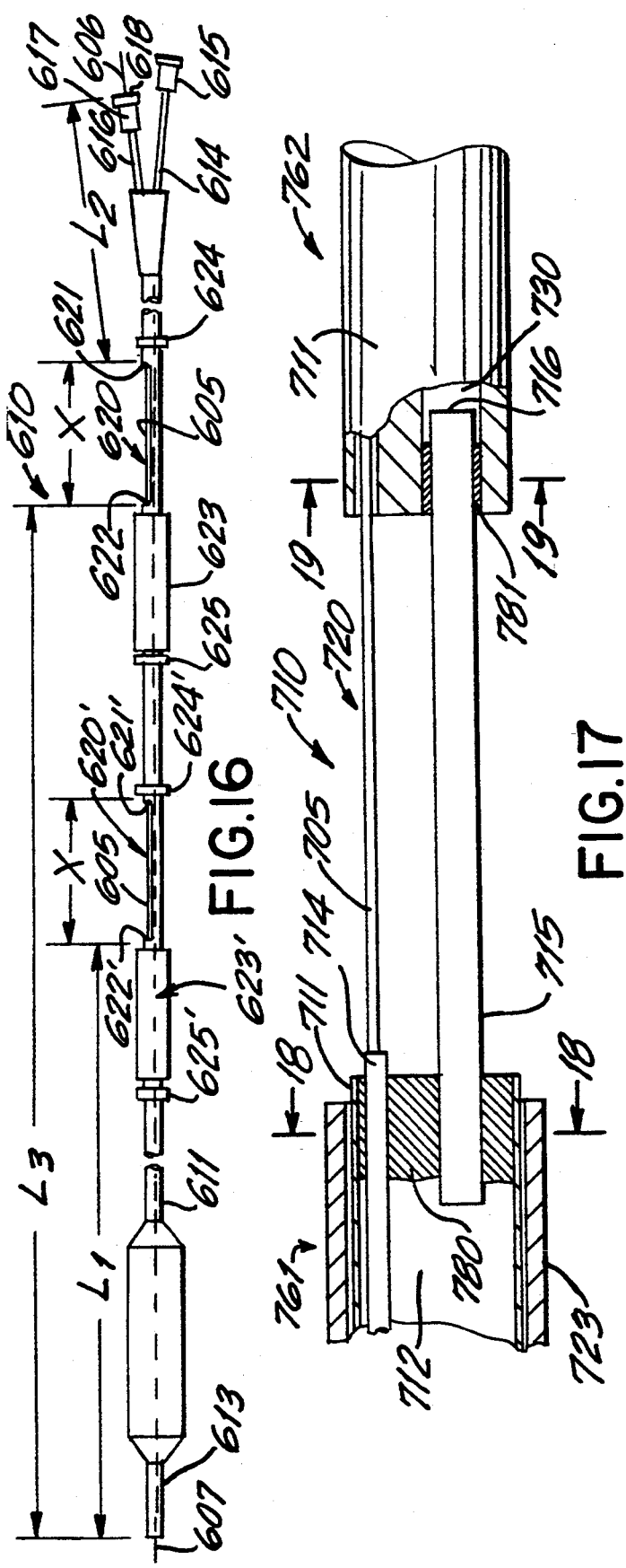
FIG. 16
FIG. 17
FIG. 18
FIG. 19

WINDOWED CATHETER AND METHOD OF USE

This is a continuation of application Ser. No. 08/030,841, filed on Mar. 12, 1993, now abandoned.

FIELD OF THE INVENTION

This invention relates to catheters placed in the body of a patient such as in the cardiovascular system and, in particular, to a catheter which permits exchange of the catheter while maintaining in the patient the guidewire over which the catheter is inserted.

BACKGROUND OF THE INVENTION

Catheters are placed at various locations within a patient for a wide variety of purposes and medical procedures. For example only, one type of catheter is a balloon dilatation catheter which is used in the treatment of a vascular stenosis. Such a catheter has a balloon at its distal end which is intended to be placed, in a deflated condition, within the stenosis, and then inflated while in the stenosis to expand radially the stenosed lumen of the blood vessel. Typically, the placement of such catheters involves the use of a guidewire which may be advanced through the patient's vasculature to the location which is to be treated. The catheter, which has a lumen adapted to receive the guidewire, is advanced over the wire which guides the catheter to the location to be treated. In so-called over-the-wire catheters, the guidewire lumen extends the entire length of the catheter and the guidewire received therein is entirely within the catheter except for the guidewire ends which extend from the distal and proximal ends of the catheter.

While over-the-wire catheters have many advantages traceable to a full-length guidewire lumen, including good stiffness and pushability and the availability of the guidewire lumen for pressure measurement and distal dye injections, such catheters do suffer some shortcomings.

For example, it is generally necessary for the guidewire and catheter to be advanced together through the guiding catheter and patient. Specifically, if the guidewire is first located across the stenosis and then the distal end of the catheter is threaded onto the proximal end of the guidewire, the physician would be unable to advance the catheter without undesirably also advancing the guidewire. That results because, unless an extension wire which can be twice the length of the catheter, is used, there is no portion of the guidewire extending out of the catheter that can be secured to ensure that only the catheter moves distally. Requiring the user to advance the catheter and guidewire together through the guiding catheter is undesirable because if it turns out that the user is not able ultimately to cross the stenosis with the guidewire, then the dilatation procedure will have to be aborted, resulting in the waste of a relatively expensive catheter.

Additionally, it often becomes necessary, in the performance of a catheter procedure, to exchange the indwelling catheter for another catheter, for example, for a catheter having a different size balloon. In one type of over-the-wire catheter exchange, the guidewire first is removed from the lumen of the indwelling catheter. Then a longer exchange wire is passed through the catheter to replace the original wire. Then, while holding the exchange wire by its proximal end to maintain it in place, the catheter is withdrawn proximally from the blood vessel over the exchange wire. After the first catheter has been removed, the next catheter is then threaded onto the proximal end of the exchange wire and is advanced along the exchange wire and through the patient's blood vessels until the distal end of the catheter is located as desired. The exchange wire may be permitted to remain in place or may be exchanged for a shorter, conventional length guidewire.

A non-over-the-wire catheter that permits the guidewire to be fully inserted into the patient before the catheter, and also permits catheter exchange while maintaining the in-situ guidewire in place is the so-called MONORAIL TM type catheter. Catheters of this type, which are described in U.S. Pat. Nos. B1 4,762,169, 5,040,548 and 5,061,273, are formed so that the guidewire is located outside of the catheter except for a short segment at the distal end of the catheter, which passes over the wire. The distal segment of the catheter has a short lumen which extends from the distal tip of the catheter to a more proximally located opening near the distal tip. In use, the guidewire is placed initially in the patient's vascular system. The distal segment of the catheter then is threaded onto the wire. The catheter can be advanced alongside the wire with its distal segment being attached to and guided along the wire. The catheter can be removed and exchanged for another catheter without the use of the usual double length exchange wire and without requiring withdrawal of the initially placed guidewire.

Although the proposed MONORAIL catheter system may avoid the requirement for using a long exchange wire, it presents several difficulties. For example, it is not possible to exchange guidewires in an indwelling catheter as can be done with over-the-wire catheters. Additionally, the device presents a potential for damaging the delicate inner surface of an artery from a tension load applied to the guidewire which would tend to straighten the artery. Also, there is an increased risk of guidewire entanglement in those procedures where multiple guidewires are used, because the guidewires are exposed within the blood vessel.

The MONORAIL catheters, which do not include a guidewire lumen for the entire length of the catheter, also lack the desired stiffness and pushability for readily advancing the catheter through tortuous blood vessels. In addition, the lack of a full length guidewire lumen deprives the physician of an additional lumen that may be used for other purposes, e.g., pressure measurement and distal dye injection.

It is among the general objects of the invention to provide an improved device which overcomes the foregoing difficulties.

SUMMARY OF THE INVENTION

In accordance with the invention, a catheter is provided for insertion into a patient over an elongated guidewire having proximal and distal ends. The catheter includes an elongated catheter shaft having open proximal and distal ends and a longitudinal guidewire lumen for receiving the guidewire and extending substantially the entire length of the catheter between the open ends of the catheter shaft. The catheter shaft has a length such that the guidewire receivable in the guidewire lumen can extend out the proximal and distal ends of the catheter. The catheter shaft further includes a window element opening the guidewire lumen to the exterior of the catheter. The window element has a proximal end and a distal end and is located on the catheter shaft and has a length such that after the catheter has been inserted to a desired location in a patient, the catheter can be withdrawn proximally over the guidewire by securing the proximal end of the guidewire, and the window can be exposed to provide access to the guidewire therethrough before the proximal end of the guidewire has been slid to a position distal of the proximal end of the catheter and such that when the catheter is further withdrawn proximally over the guidewire, the distal end of the catheter becomes exposed to provide access to the guidewire extending therefrom before the proximal end of the guidewire is slid to a position distal of the distal end of the window.

In another embodiment, the catheter of the invention may include a plurality of window elements including a first window element which is located on the shaft and has a length such that after the catheter has been inserted to a desired location in the patient, the catheter can be withdrawn proximally over the guidewire by securing the proximal end of the guidewire, and the first window can be exposed to provide access to the guidewire therethrough before the proximal end of the guidewire has been slid to a position distal of the proximal end of the catheter. One of the other windows is located distal of said first window and has such a length that when the catheter is further withdrawn proximally over the guidewire, the other window is exposed to provide access to the guidewire through the other window before the proximal end of the guidewire is slid to a position distal of the first window and such that before the proximal end of the guidewire has been slid distally of all of the plurality of windows, the distal end of the catheter has been exposed to provide access to the guidewire extending therefrom so that the guidewire may be secured at the distal end of the catheter and the catheter fully withdrawn over the guidewire.

The present invention further includes various methods for first inserting the guidewire to a desired location in the patient and then advancing the catheter over the guidewire by manipulating the guidewire through one or more window elements on the catheter shaft. The invention further includes various methods for withdrawing the catheter over the indwelling guidewire while maintaining the guidewire in place by manipulating the guidewire through one or more windows on the catheter shaft.

BRIEF DESCRIPTION OF THE DRAWINGS

FIG. 1 is an elevational view of the windowed catheter of the subject invention.

FIG. 2 is an enlarged view of the window portion of the catheter shown in FIG. 1.

FIG. 3 is a cross-sectional view taken along line 3—3 of FIG. 2.

FIG. 4 is a cross-sectional view taken along line 4—4 of FIG. 2.

FIG. 5 is a cross-sectional view taken along line 5—5 of FIG. 2.

FIG. 6 is an enlarged partial elevational view of the window portion of another embodiment of the subject invention.

FIG. 7 is a cross-sectional view taken along line 7—7 of FIG. 6.

FIG. 8 is a cross-sectional view taken along line 8—8 of FIG. 6.

FIG. 9 is a cross-sectional view taken along line 9—9 of FIG. 6.

FIG. 16 is an elevational view of a double window embodiment of the subject catheter.

FIG. 17 is an enlarged elevational view of the window portion of another embodiment of the subject catheter.

FIG. 18 is a cross-sectional view taken along line 18—18 of FIG. 17.

FIG. 19 is a cross-sectional view taken along line 19—19 of FIG. 17.

DETAILED DESCRIPTION OF THE PREFERRED EMBODIMENTS

Figure 10:
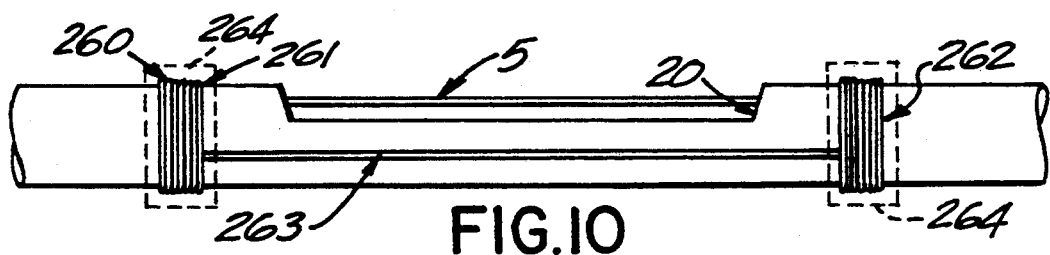
FIG. 10 is a partial enlarged elevational view of the window portion of the catheter of FIG. 1 showing a modified reinforcement means.

Referring to FIGS. 1-5, there is illustrated a first embodiment of the subject invention. It should be noted that while the figures and the following description are directed to over-the-wire balloon dilatation catheters, and particularly coronary angioplasty dilatation catheters, the invention is not necessarily so limited and is applicable to other types of over-the-wire catheters wherein it is desired to exchange the catheter while maintaining the in-situ guidewire in place, without the need for extension wires.

As illustrated in FIGS. 1-5, the catheter of the invention, which is designated generally as 10, includes an elongated shaft 11 having an open distal end 13 and an open proximal end 12 defined by a guidewire leg 17, a fitting 17a and a proximal guidewire port 18. As shown, the catheter also includes an inflation leg 19 having a proximal inflation port 19a. The catheter shaft 11 may be extruded to form two side-by-side lumens, namely, a guidewire lumen 14 and an inflation lumen 15, both of which extend at least substantially the entire length of the catheter. As shown, the guidewire lumen 14 extends the entire length of the catheter, from distal end 13 to proximal end 12 and guidewire leg 17, fitting 17a and guidewire port 18. The length of the catheter relative to the guidewire is such that when a guidewire 5 is received in guidewire lumen 14, the distal end 7 of the guidewire extends out the distal end 13 of the catheter, and the proximal end 6 if the guidewire extends out the proximal end 12 and guidewire port 18 of the catheter. Although not specifically shown, the inflation lumen has a distal end that terminates within or at the proximal end of an inflatable balloon 16.

As shown, the catheter 10 is an over-the-wire type catheter, with the guidewire being disposed within the catheter shaft and its guidewire lumen for substantially the length of the catheter. In addition, because the catheter includes a guidewire lumen 14 that extends the entire length of the catheter, that lumen 14, aside from receiving the guidewire 5, is available for other purposes such as pressure measurement or serving as a conduit for some fluid, such as contrast dye.

In accordance with the invention, the catheter shaft 11 includes a window element 20 that exposes the guidewire lumen 14 and guidewire 5 to the exterior of the catheter so as to make the guidewire accessible for manipulation during a catheter insertion and/or exchange as will be described below. The window 20 has a proximal end 21 and a distal end 22 and defines a catheter portion 11a of reduced diameter. The window element 20 is of such a length and is located on the catheter shaft that after the catheter 10 has been fully inserted into a patient over guidewire 5, the catheter can be withdrawn proximally over guidewire 5 by securing the proximal end 6 of the guidewire and window 20 can be exposed to provide access to the guidewire therethrough before the proximal end 6 of the guidewire has been slid to a position distal of the proximal end of the catheter defined by port 18.

In addition, the window 20 has such a length and is so located on the catheter shaft that when the catheter has been further withdrawn proximally over the guidewire 5 such that the distal end 13 of the catheter is disposed outside the patient so as to expose a portion of the guidewire extending out the distal end 13 of the catheter before the proximal end 6 of the guidewire is slid to a position distal of window 20.

In the preferred embodiment of the invention, the catheter 10 further includes a sleeve member 23 that is slidably disposed on the catheter shaft 11 to selectively open and close the window 20. Sleeve 23 is preferably relatively thin in thickness so as not to present too much of a discontinuity on the catheter exterior surface. Sleeve 23, which has a proximal end 27 and a distal end 28, also preferably has a length greater than that of the window 20 so that the sleeve can fully close window 20 and guidewire 5 and guidewire lumen 14. In addition, it is preferable that the catheter shaft 11 include a first proximal stop member 24 for engaging proximal end 27 of sleeve 23 and preventing further proximal movement of the sleeve along shaft 11, and a second distal stop member 25 for engaging the distal end 28 of sleeve 23 and preventing further distal movement of the sleeve along the shaft 11. The stops 24 and 25 also provide tactile indication to the user when the window 20 is in the closed or open position, respectively.

As illustrated in FIG. 2, it may be desirable for the catheter to include means for reinforcing the catheter shaft adjacent to the window 20 where the shaft is of reduced diameter. Such reinforcement means may comprise a wire 26 that is helically wrapped around and preferably bonded to the shaft both proximal and distal to the window 20 and along the shaft portion 11a of reduced diameter.

FIG. 10 shows an alternate form of reinforcement means wherein a support wire 260 is wrapped around and preferably bonded to the catheter shaft several times both distal and proximal to the window 20 to form distal and proximal windings 261 and 262 respectively and a longitudinal wire portion 263 extending between windings 261 and 262. Windings 261 and 262 may be bonded to the catheter shaft with or without a plastic band 264.

Figure 11:
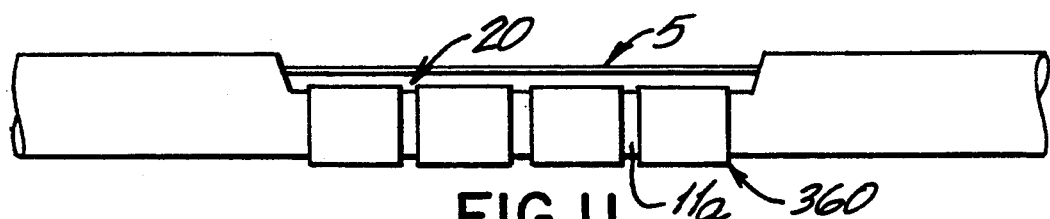
FIG. 11 is an enlarged partial elevational view of the window portion of the catheter of FIG. 1 showing another form of reinforcement means.

FIG. 11 shows a further alternate embodiment of a reinforcement means which comprises a plurality of generally semi-circular tubular elements 360 disposed around the catheter shaft portion of reduced diameter 11a. Elements 360 may comprise adhesive lined shrink tubing that is spaced appropriately to maximize flexibility and shaft strength.

As discussed above, window element 20 has a length and a location on the catheter shaft that enables the catheter to be fully withdrawn over the in-situ guidewire while keeping the guidewire in place within the patient. By way of example only, and not as a limitation on the invention, it has been found that the following dimensions are viable:

| Guidewire LENGTH | $L_1$ | $L_2$ | X |
| --- | --- | --- | --- |
| 180 | 55 cm | 55 cm | 33 cm |
| 190 | 65 cm | 65 cm | 13 cm |
| 200 | 75 cm | 75 cm | 10 cm | where
 $L_1$ is the length of the catheter 10 from the tip of distal end 13 to the distal end 22 of window 20;
 $L_2$ is the length of catheter 10 from the proximal end 21 of window 20 to proximal port 18; and
 X is the length of window 20.

The above dimensions assume a 100 cm guiding catheter, a 20 cm portion of the guidewire extending out the distal end of the guiding catheter, and a 143 cm catheter 10 (from distal end 13 to port 18).

FIGS. 6–9 illustrate another embodiment of the subject catheter which is designated generally as 210. As with FIGS. 1–5, only the window portion of the catheter is shown in FIGS. 6–9, the remaining portions of the catheter being essentially the same as shown in FIGS. 1–5.

Referring to FIGS. 6–9, the catheter 210 includes an elongated catheter shaft 211 having a coaxial central lumen 212 which may communicate with a source of inflation fluid. Disposed within central lumen 212 is a guidewire tube 214 which defines a guidewire lumen 214a which extends substantially the entire length of the catheter for slidably receiving a guidewire 205. As shown, guidewire tube 214 is bonded and sealed within catheter shaft 211 with adhesive 280.

In accordance with the invention, catheter 210 includes a window element 220 having a proximal end 221 and a distal end 222. As shown, the portion of the guidewire tube 214 that is disposed within window 220 is cut to expose guidewire 205 within the window. The catheter 210 further includes a sleeve member 223 that is slidably disposed on the catheter shaft 211 to selectively open and close the window 220.

Catheter 210 also includes an inflation tube 215 which defines an inflation lumen 215a which communicates with central lumen 212 and which is disposed within window 220 and extends beyond the proximal and distal ends 221 and 222, respectively, of the window. As shown, inflation tube 215 is arranged in side-by-side relationship with guidewire tube 214 and is bonded and sealed within the catheter shaft with adhesive 280. Adhesive 280 provides seals for ensuring that all the inflation fluid passing through lumen 212 flows through inflation tube 215 and not out window 220.

Figure 12:
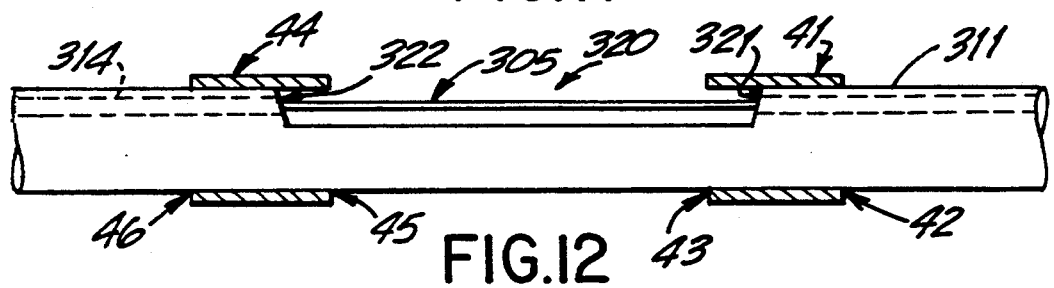
FIG. 12 is an enlarged partial elevational view of the window portion of another embodiment of the subject catheter.

FIG. 12 illustrates another embodiment of the window portion of the subject catheter. In this embodiment, the catheter which is designated generally as 310 includes a catheter shaft 311 having a guidewire lumen 314 extending substantially the entire length of the catheter for slidably receiving a guidewire 305. The catheter shaft 311 includes a window element 320 having a proximal end 321 and a distal end 322. In this embodiment, instead of a slidable sleeve for selectively closing and opening the window 320, the catheter includes a proximal alignment sleeve 41 fixed to the catheter shaft and having a proximal end 42 and a distal end 43. In accordance with the invention, the distal end 43 of sleeve 41 extends distally beyond the proximal end 321 of window 320 into the window. The portion of sleeve 41 extending into the window facilitates the aligning of guidewire 305 in the guidewire lumen.

Preferably catheter 310 also includes a distal alignment sleeve 44 which is fixed to catheter shaft 311 and has a proximal end 45 and a distal end 46. In accordance with the invention, the proximal end 45 of sleeve 44 extends proximally beyond distal window end 322 and into window 320. The portion of sleeve 44 extending into window 320 also facilitates in aligning guidewire 305 into the guidewire lumen.

Figure 13:
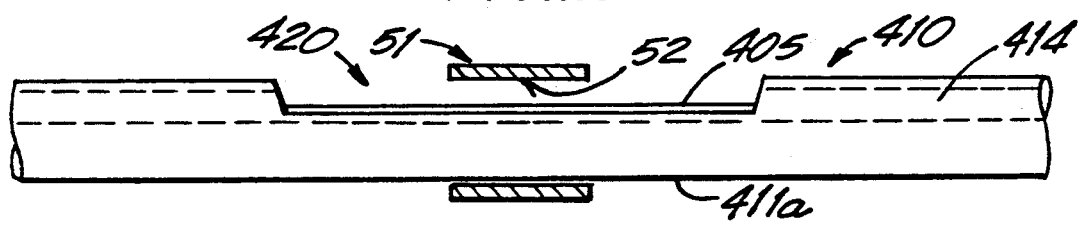
FIG. 13 is an enlarged partial elevational view of the window portion of another embodiment of the subject catheter.

FIG. 13 illustrates a variation on the alignment sleeve concept of FIG. 12. In FIG. 13, the catheter 410 includes an alignment sleeve 51 that is slidably disposed around the catheter portion of reduced diameter 411a defined by window element 420. Alignment sleeve 51 defines an alignment channel 52 for facilitating alignment of guidewire 405 with the guidewire lumen 414.

Figure 14:
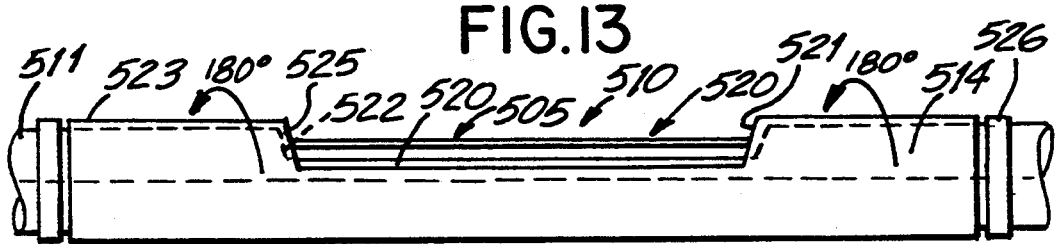
FIG. 14 is an enlarged partial elevational view of the window portion of another embodiment of the subject catheter with the window being in the open position.
Figure 15:
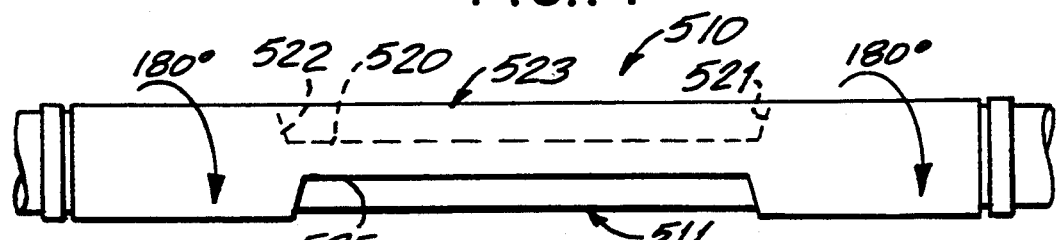
FIG. 15 is a view similar to that shown in FIG. 14 with the window being in the closed position.

FIGS. 14 and 15 illustrate an alternate embodiment of the sleeve for opening and closing the catheter window. As shown, catheter 510 includes a catheter shaft 511 having a guidewire lumen 514 extending substantially the entire length of the catheter for slidably receiving a guidewire 505. The catheter includes a window element 520 for exposing the guidewire 505. The catheter also includes a sleeve member 523 that is rotatably disposed over the catheter shaft 511. Preferably, stops 526 and 527 are disposed around catheter shaft 511 on either side of sleeve 523 to keep sleeve 523 in place.

Sleeve 523 includes a window member 525. As illustrated in FIG. 14, sleeve window 525 is aligned with catheter window 520, which has a proximal end 521 and a distal end 522, to open window 520 and expose guidewire 505.

FIG. 15 shows sleeve 523 after it has been rotated 180° from the position shown in FIG. 14. As shown in FIG. 15, sleeve window 525 is no longer aligned with catheter window 520 such that the catheter window is effectively closed.

Another option from the slidable sleeve of FIGS. 1-9 and the rotatable sleeve of FIGS. 14-15 is a thin tube, e.g., a shrink tube, that is fixed around the catheter shaft and window which may be slit open when access to the window and the guidewire disposed therein is desired or which contains a guidewire port aligned with the window for that purpose.

The preferred methods for using the catheters of FIGS. 1-15 will now be discussed. It should be noted that while the methods will be described with particular reference to the catheter of FIGS. 1-5, the method described will be equally applicable by one of ordinary skill in the art to the catheters of FIGS. 6-15.

Preparatory to insertion into a patient, the catheter window 20 is closed by sliding sleeve 23 proximally until sleeve 23 engages stop 24. The guidewire 5 is loaded into the guidewire lumen 14 of the catheter and both may be inserted together into the patient in the usual way. When fully inserted into the patient, the proximal and distal ends of the guidewire 6 and 7, respectively, extend beyond the proximal and distal ends 12 and 13, respectively, of the catheter.

Alternatively, and as a result of the unique construction of the subject catheter, the guidewire may be inserted and located at the desired position within the patient before the sterile package containing the catheter is opened. After the guidewire has been successfully located in the patient, the catheter may be extracted from its package and the window 20 opened by sliding sleeve 23 distally until it engages stop 25. The proximal end 6 of the guidewire, which extends out of the patient and the guiding catheter so as to be exposed, is threaded into the distal end 13 of the catheter and into the guidewire lumen. As the exposed guidewire disposed distal of the catheter is gripped, the catheter is advanced distally. In accordance with the invention, the proximal end of the guidewire will be disposed within the open catheter window 20 before the distal end of the catheter is received in and enclosed by the guiding catheter and the patient. The guidewire is then exposed from window 20 by gripping both ends of the window and pushing inwardly. With one hand holding the guidewire distally inside window 20 while holding the distal end 22 of the window, the other hand slides the proximal end 21 of the window distally along a portion of the length of the guidewire, e.g., typically until about one inch of the guidewire is still exposed from window 20. This creates a bowing effect of the window. The guidewire is then held with one hand proximally inside the window while holding the proximal end of the window and the other hand slides the distal end of the window distally along a portion of the guidewire, i.e., until the window straightens out. The above steps are repeated until the proximal end of the guidewire exits the proximal end of the catheter. Window 20 may then be closed by sliding sleeve 23 proximally until it engages stop 24. The proximal end of the guidewire may then be gripped and the catheter slid distally until it reaches the desired position within the patient.

To effect catheter exchange, the proximal end 6 of the guidewire is gripped and the catheter slid proximally. In accordance with the invention, the window 20 will be disposed outside of the patient and guiding catheter and, thus exposed before the proximal end of the guidewire is slid to a position distal of the proximal end port 18 of the catheter. The window may then be opened by sliding sleeve 23 distally until it engages stop 25. The guidewire 5 may be exposed from the window 20 by pushing the ends of the window toward each other. With one hand holding the guidewire proximally inside window 20 while simultaneously holding the proximal end 21 of window 20, the other hand slides the distal end 22 of the window proximally along the guidewire to withdraw the catheter a portion of the guidewire length, e.g., until about one inch of the guidewire is still exposed. This creates a bowing of the window. Then holding the guidewire distally inside the window with one hand while holding the distal end of the window, the other hand slides the proximal end of the window proximally another portion of the length of the guidewire, e.g., until the window straightens out. The above steps are repeated until the distal end of the catheter is disposed exterior to the patient and guiding catheter such that a portion of the guidewire extending distally beyond the distal end of the catheter may be secured and the catheter fully withdrawn over the proximal end of the guidewire.

Another method of withdrawing the subject catheter while maintaining the guidewire in place within the patient comprises the steps of gripping the guidewire at the proximal end 21 of window 20 and pulling the catheter down the guidewire until the user's grip comes into contact with the distal end 22 of the window, at which point the catheter cannot be pulled down any further. The user then again grips the guidewire at the proximal end 21 of the window and pulls the catheter down the guidewire again until his grip comes into contact with the distal end 22 of the window. The above procedure is repeated until the distal end of the catheter is exposed outside the patient's body. Thereafter, the physician can grab the guidewire distal of the distal end of the catheter and pull the entire catheter off the guidewire. It should be noted that another method of inserting the catheter into the patient comprises performing the above steps in reverse.

FIG. 16 illustrates another embodiment of the subject catheter which includes a plurality of window elements. While the catheter, which is designated generally as 610, will be described simply in the context of the plurality window feature, it will be understood that all of the elements discussed above with respect to FIGS. 1-5 may be included in catheter 610.

Turning now specifically to FIG. 16, catheter 610 includes an elongated shaft 611 having a proximal end 612 defined by a hollow guidewire leg 616, fitting 617 and port 618. The catheter also includes a hollow inflation leg 614 and fitting 615.

The catheter 610 includes a guidewire lumen that extends substantially the entire length of the catheter, from distal end 613 to proximal end 612 and port 618, for slidably receiving a guidewire 605 such that the proximal end 606 of the guidewire extends out the proximal end of the catheter, and specifically out of port 618, and the distal end 607 of the guidewire extends out the distal end 613 of the catheter.

The catheter shaft 611 includes a first window element 620 disposed adjacent to the proximal end of the catheter having a proximal end 621 and a distal end 622. Window 620 communicates with the guidewire lumen of the catheter to expose the guidewire 605 to the exterior of the catheter. Preferably, the catheter also includes a first window sleeve 623 to selectively open and close window 620. Preferably, proximal and distal stops 624 and 625, respectively, are disposed on the catheter shaft to help locate sleeve 623 in the open and closed positions, respectively.

In accordance with the invention, the catheter shaft 611 further includes a second window element 620' having a proximal end 621' and a distal end 622'. Window 620' communicates with the guidewire lumen of the catheter to expose the guidewire 605 to the exterior of the catheter. Preferably, the catheter also includes a second window sleeve 623' slidably disposed around the catheter shaft to selectively open and close window 620'. Preferably, proximal and distal stops 624' and 625', respectively, are disposed on the catheter shaft to help locate sleeve 623' in the open and closed positions, respectively.

By way of example only, and not as a limitation on the invention, it has been found that the following dimensions are viable:

| Guidewire LENGTH | $L_1$ | $L_2$ | $L_3$ | X |
|---|---|---|---|---|
| 180 | 55 cm | 55 cm | 78 cm | 10 cm | where $L_1$ is the length of the catheter 610 from the tip of distal end 613 to the distal end 622' of window 620';

$L_2$ is the length of the catheter 610 from the proximal end 621 of window 620 to the proximal end port 618 of fitting 617;

$L_3$ is the length from the tip of distal end 613 of the catheter to the distal end 622 of window 620; and X is the length of the windows 620' and 620.

The above dimensions assume a 100 cm guiding catheter, a 20 cm portion of the guidewire extending out the distal end of the guiding catheter, and a 143 cm catheter from the tip of distal end 613 to proximal port 618.

The preferred methods for using the catheters of FIG. 16 will now be discussed.

Preparatory to insertion into a patient, the catheter windows 620 and 620' may be closed by sliding sleeves 623 and 623' proximally until sleeve 623 engages stop 624' and sleeve 623 engages stop 624. The guidewire 605 is loaded into the guidewire lumen of the catheter and the catheter and guidewire may be inserted into the patient together in the usual way. When fully inserted into the patient, the proximal and distal ends of the guidewire 606 and 607, respectively, extend beyond the proximal and distal ends of the catheter.

Alternatively, and as a result of the unique construction of the subject catheter, the guidewire may be inserted and located at the desired position within the patient before the sterile package containing the catheter is opened. After the guidewire has been successfully located in the patient, the catheter may be extracted from its package and the windows 620 and 620' opened by sliding sleeves 623 and 623' distally until they engage stops 625 and 625'. The proximal end 606 of the guidewire, which extends out of the patient and the guiding catheter so as to be exposed, is threaded onto the distal end 613 of the catheter and into the guidewire lumen. As the exposed guidewire disposed distal of the catheter is gripped, the catheter is advanced distally.

In accordance with the invention, the proximal end of the guidewire will be disposed within the open catheter window 620' before the distal end of the catheter is received in and enclosed by the guiding catheter and the patient. The guidewire is then exposed from window 620' by gripping both ends of the window and pushing inwardly. With one hand holding the guidewire distally inside window 620' while holding the distal end 622' of the window, the other hand slides the proximal end 621' of the window distally along a portion of the length of the guidewire, e.g., typically until about one inch of the guidewire is still exposed from window 620'. This creates a bowing effect of the window. The guidewire is then held with one hand proximally inside the window while holding the proximal end of the window and the other hand slides the distal end of the window distally along a portion of the guidewire, i.e., until the window straightens out. The above steps are repeated until the proximal end of the guidewire is disposed within window 620. Window 620' may then be closed by sliding sleeve 623' proximally until it engages stop 624'. The above steps are repeated by manipulating the guidewire and the proximal and distal ends of window 620 until the proximal end of the guidewire exits the proximal end of the catheter. Window 620 may then be closed by sliding sleeve 623 proximally until it engages stop 624. The proximal end of the guidewire may then be gripped and the catheter slid distally until it reaches the desired position within the patient.

To effect catheter exchange, the proximal end 606 of the guidewire is gripped and the catheter slid proximally. In accordance with the invention, the window 620 will be disposed outside of the patient and guiding catheter and, thus exposed before the proximal end of the guidewire is slid to a position distal of the proximal end port 618 of the catheter. The window may then be opened by sliding sleeve 623 distally until it engages stop 625. The guidewire 605 may be exposed from the window 620 by pushing the ends of the window toward each other. With one hand holding the guidewire proximally inside window 620 while simultaneously holding the proximal end 621 of window 620, the other hand slides the distal end 622 of the window proximally along the guidewire to withdraw the catheter a portion of the guidewire length, e.g., until about one inch of the guidewire is still exposed. This creates a bowing of the window. Then holding the guidewire distally inside the window with one hand while holding the distal end of the window, the other hand slides the proximal end of the window proximally another portion of the length of the guidewire, e.g., until the window straightens out. The above steps are repeated until window 620' is disposed exteriorally of the patient and guiding catheter and thus exposed. Window 620' may be opened by sliding sleeve 623' distally until it engages stop 625'. The above withdrawal steps are repeated by manipulating the guidewire and the proximal and distal ends of window 620' until the distal end of the catheter is disposed exterior to the patient and guiding catheter such that a portion of the guidewire extending distally beyond the distal end of the catheter may be secured and the catheter fully withdrawn over the proximal end of the guidewire.

Another method of withdrawing the subject catheter while maintaining the guidewire in place within the patient comprises the steps of gripping the guidewire at the proximal end 621 of window 620 and pulling the catheter down the guidewire until the user's grip comes into contact with the distal end 622 of the window, at which point the catheter cannot be pulled down any further. The user then again grips the guidewire at the proximal end 621 of the window and pulls the catheter down the guidewire again until his grip comes into contact with the distal end 622 of the window. The above procedure is repeated until window 620' is exposed and opened. The above withdrawal steps may then be repeated by manipulating the guidewire and proximal and distal ends of window 620' until the distal end of the catheter is exposed outside the patient's body. Thereafter, the physician can grab the guidewire distal of the distal end of the catheter and pull the entire catheter off the guidewire. It should be noted that an alternate method for inserting the catheter into the patient comprises performing the above steps in reverse.

FIGS. 17-19 illustrate a further embodiment of the subject invention which is a variation on the shaft constructions shown in FIGS. 1-9. Again, for the sake of simplicity, only the window portion of the catheter will be described. All other elements will be the same as those described earlier.

Referring now to FIGS. 17-19, the catheter, which is designated generally as 710, includes an elongated shaft 711 which includes a guidewire lumen 714a that extends the entire length of the catheter for slidably receiving a guidewire 705. The length of the catheter relative to the guidewire is such that the guidewire extends through the catheter and out the proximal and distal ends of the catheter.

In accordance with the invention, the catheter shaft includes a window element 720 that exposes guidewire tube 714 to the exterior of the catheter. The catheter 710 further includes a sleeve member 723 that is slidably disposed on the catheter shaft 711 to selectively open and close the window 720. In addition, the portion of guidewire tube 714 disposed within window 720 is cut open to expose guidewire 705 to the exterior of the catheter.

Catheter 710 also includes an inflation tube 715 having an inflation lumen 715a, inflation tube 715 bridging window 720.

As illustrated in FIGS. 17-19, window 720 divides the catheter shaft into a distal portion 761 and a proximal portion 762. Distal portion 761 includes a central lumen 712 which is coaxial with shaft 711. Within distal shaft portion 761, the guidewire lumen 714a is defined by a guidewire tube 714 which is disposed in central lumen 712 and which extends from the distal end of the catheter to window 720. Guidewire tube 714 is fixed within lumen 712 by an adhesive 780.

A portion of inflation tube 715 is also fixed within lumen 712 by adhesive 780, the inflation lumen 715a defined by tube 715 communicating with lumen 712 which is connected to an inflatable balloon disposed on the distal end of the catheter. In addition to fixing tubes 714 and 715 within catheter lumen 712, adhesive 780 effects a sealing of lumen 712 to ensure that all the inflation fluid flows through inflation tube 715, lumen 712 and the balloon disposed on the distal end of the catheter and not out window 720.

The catheter proximal shaft portion 762 is a dual lumen extrusion which defines guidewire lumen 714a extending from the proximal end 721 of window 720 to the proximal end of the catheter, and a fluid lumen 730 extending from the proximal end 716 of inflation tube 715 to the proximal end and inflation port of the catheter. Inflation lumen 715a communicates with fluid lumen 730 which in turn communicates with a source of inflation fluid. Proximal end 716 of inflation tube 715 is adhered to the catheter by adhesive 781, which also effects a seal ensuring that the inflation fluid from lumen 730 passes through inflation tube 715 and not out window 720.

Because of its two shaft portion construction, catheter 710 has increased flexibility in its distal portion and increased stiffness in its proximal portion.

It should be noted, however, that the catheter shaft may include different combinations of coaxial and extruded portions than that shown in FIGS. 17-19, depending upon the particular application. And, any of such catheter shafts may employ the single or plural window concept of the subject invention. In addition, it should be noted that catheter 710 may include a sleeve 713 slidably disposed over the catheter shaft 711 to selectively open or close window 720.

Various changes and modifications to the embodiments shown in the drawings and described above may be made within the scope of the invention. Therefore, it is intended that all matter contained in the above description and shown in the accompanying drawings shall be interpreted in an illustrative and not limiting sense.

What is claimed is:

1. A catheter for insertion into a patient over an elongated guidewire having proximal and distal ends, comprising:

an elongated guidewire; and an elongated catheter shaft having open proximal and distal ends and a longitudinal guidewire lumen for receiving the guidewire and extending substantially the entire length of the catheter between the open ends of the catheter shaft, the catheter shaft having a length relative to the guidewire such that the guidewire, when received in said lumen, can extend out the proximal and distal ends of the catheter, said catheter shaft further including a window element opening the guidewire lumen to the exterior of the catheter, the window element having a proximal end and a distal end, the window element being located on the catheter shaft and having a length such that after the catheter and guidewire have been fully inserted into the patient, the catheter can be withdrawn proximally over the indwelling guidewire and the window can be exposed so as to provide access to the guidewire therethrough before the proximal end of the guidewire is disposed distal to the proximal end of the catheter, and said catheter element length such that after the catheter and guidewire have been fully inserted into the patient said catheter can also be withdrawn proximally over the indwelling guidewire so that the distal end of the catheter is disposed outside of the patient so as to expose and render accessible a portion of the guidewire extending from the distal end of the catheter before the proximal end of the guidewire is disposed distal to the window element.

2. A catheter according to claim 1 which further includes an inflatable balloon member disposed on the distal end of the catheter and an inflation lumen extending the length of the catheter and communicating with said balloon, the guidewire lumen and inflation lumen being disposed in side-by-side relationship to one another.

3. A catheter according to claim 1 wherein the catheter shaft further includes reinforcement means disposed adjacent the window element.

4. A method for withdrawing a catheter over a guidewire disposed within a patient while maintaining the guidewire in place in the patient, the guidewire having a proximal end and a distal end, the catheter having an elongated shaft having open proximal and distal ends and a longitudinal guidewire lumen for receiving the guidewire and extending substantially the entire length of the catheter between the open ends of the catheter shaft, the catheter shaft having a length such that the guidewire receivable in said lumen can extend simultaneously out the proximal and distal ends of the catheter, said catheter shaft further including a window element opening the guidewire lumen to the exterior of the catheter, the window element having a proximal end and a distal end, the window element being located on the catheter shaft and having a length such that after the catheter is inserted into the patient, the catheter can be withdrawn proximally over the guidewire and said window element can be exposed so as to provide access to the guidewire therethrough before the proximal end of the guidewire is disposed distal to the proximal end of the catheter and such that said catheter can also be withdrawn proximally over the guidewire so that the distal end of the catheter is outside of the patient so as to expose and render accessible a portion of the guidewire extending from the distal end of the catheter before the proximal end of the guidewire is disposed distal to the window element, comprising the steps of:

(a) grasping the proximal end of the guidewire and withdrawing the catheter proximally along the guidewire as much as possible so as to expose the window and render it accessible;

(b) holding the guidewire proximally inside the window while holding the proximal end of the window;

(c) sliding the distal end of the window proximally along a portion of the guidewire;

(d) holding the guidewire distally inside the window while holding the distal end of the window;

(e) sliding the proximal end of the window proximally along a portion of the guidewire;

(f) repeating steps (b) through (e) until the distal end of the catheter is exposed and the guidewire extending therefrom accessible; and (g) grasping the guidewire distal of the distal end of the catheter and pulling the catheter off the proximal end of the guidewire.

5. A method for inserting an over-the-wire catheter into a patient over a guidewire, the guidewire having a proximal end and a distal end, the catheter having an elongated shaft having open proximal and distal ends and a longitudinal guidewire lumen for receiving the guidewire and extending substantially the entire length of the catheter between the open ends of the catheter shaft, the catheter shaft having a length such that the guidewire receivable in said lumen can extend simultaneously out the proximal and distal ends of the catheter, said catheter shaft further including a window element opening the guidewire lumen to the exterior of the catheter, the window element having a proximal end and a distal end, the window element being located on the catheter shaft and having a length such that after the catheter is inserted into the patient, the catheter can be withdrawn proximally over the guidewire and said window element can be exposed so as to provide access to the guidewire therethrough before the proximal end of the guidewire is disposed distal to the proximal end of the catheter and such that said catheter can also be withdrawn proximally over the guidewire so that the distal end of the catheter is outside of the patient so as to expose and render accessible a portion of the guidewire extending from the distal end of the catheter before the proximal end of the guidewire is disposed distal to the window element, comprising the steps of:

(a) inserting the proximal end of the guidewire into the distal end and guidewire lumen of the catheter;

(b) gripping the guidewire disposed distal to the catheter and advancing the catheter distally over the guidewire until the guidewire is disposed within the catheter window;

(c) holding the guidewire distally inside the window while holding the distal end of the window;

(d) sliding the proximal end of the window distally along a portion of the guidewire;

(e) holding the guidewire proximally inside the window while holding the proximal end of the window;

(f) sliding the distal end of the window distally along a portion of the guidewire;

(g) repeating steps (c) through (f) until the proximal end of the guidewire exits the proximal end of the catheter; and (h) gripping the proximal end of the guidewire and advancing the catheter distally to a desired location in the patient.

6. A method for inserting an over-the-wire catheter into a patient over a guidewire, the guidewire having a proximal end and a distal end, the catheter having an elongated shaft having open proximal and distal ends and a longitudinal guidewire lumen for receiving the guidewire and extending substantially the entire length of the catheter between the open ends of the catheter shaft, the catheter shaft having a length such that the guidewire receivable in said lumen can extend simultaneously out the proximal and distal ends of the catheter, said catheter shaft further including a window element opening the guidewire lumen to the exterior of the catheter, the window element having a proximal end and a distal end, the window element being located on the catheter shaft and having a length such that after the catheter is inserted into the patient, the catheter can be withdrawn proximally over the guidewire and said window element can be exposed so as to provide access to the guidewire therethrough before the proximal end of the guidewire is disposed distal to the proximal end of the catheter and such that said catheter can also be withdrawn proximally over the guidewire so that the distal end of the catheter is outside of the patient so as to expose and render accessible a portion of the guidewire extending from the distal end of the catheter before the proximal end of the guidewire is disposed distal to the window element, comprising the steps of:
 (a) inserting the proximal end of the guidewire into the distal end and guidewire lumen of the catheter;
 (b) gripping the guidewire disposed distal to the catheter and advancing the catheter distally over the guidewire until the guidewire is disposed within the catheter window;
 (c) holding the guidewire at the distal end of the window;
 (d) sliding the catheter distally along a portion of the guidewire;
 (e) repeating steps (c) and (d) until the proximal end of the guidewire exits the proximal end of the catheter; and
 (f) gripping the proximal end of the guidewire and advancing the catheter distally to a desired location in the patient.

7. A method for withdrawing a catheter over a guidewire disposed within a patient while maintaining the guidewire in place in the patient, the guidewire having a proximal end and a distal end, the catheter having an elongated shaft having open proximal and distal ends and a longitudinal guidewire lumen for receiving the guidewire and extending substantially the entire length of the catheter between the open ends of the catheter shaft, the catheter shaft having a length such that the guidewire receivable in said lumen can extend simultaneously out the proximal and distal ends of the catheter, said catheter shaft further including a window element opening the guidewire lumen to the exterior of the catheter, the window element having a proximal end and a distal end, the window element being located on the catheter shaft and having a length such that after the catheter is inserted into the patient, the catheter can be withdrawn proximally over the guidewire and said window element can be exposed so as to provide access to the guidewire therethrough before the proximal end of the guidewire is disposed distal to the proximal end of the catheter and such that said catheter can also be withdrawn proximally over the guidewire so that the distal end of the catheter is outside of the patient so as to expose and render accessible a portion of the guidewire extending from the distal end of the catheter before the proximal end of the guidewire is disposed distal to the window element, comprising the steps of:
 (a) grasping the proximal end of the guidewire and withdrawing the catheter proximally along the guidewire as much as possible so as to expose the window and render it accessible;
 (b) holding the guidewire at the proximal end of the window;
 (c) sliding the catheter proximally along a portion of the guidewire;
 (d) repeating steps (b) and (c) until the distal end of the catheter is exposed and the guidewire extending therefrom accessible; and
 (e) grasping the guidewire distal of the distal end of the catheter and pulling the catheter off the proximal end of the guidewire.

8. A catheter for insertion into a patient over an elongated guidewire having proximal and distal ends, comprising:
 an elongated catheter shaft having open proximal and distal ends, a longitudinal inflation lumen extending the entire length of the catheter between the open ends of the catheter shaft, a longitudinal guidewire lumen for receiving the guidewire and extending substantially the entire length of the catheter between the open ends of the catheter shaft and the inflation lumen and guidewire lumen being disposed in side-by-side relationship to one another, the catheter shaft having a length relative to the guidewire such that the guidewire receivable in said lumen can extend out the proximal and distal ends of the catheter, said catheter shaft further including a window element opening the guidewire lumen to the exterior of the catheter, the window element having a proximal end and a distal end, the window element being located on the catheter shaft and having a length such that after the catheter has been inserted into the patient, the catheter can be withdrawn proximally over the guidewire and the window can be exposed so as to provide access to the guidewire therethrough before the proximal end of the guidewire is disposed distal to the proximal end of the catheter and such that said catheter can also be withdrawn proximally over the guidewire so that the distal end of the catheter is disposed outside of the patient so as to expose and render accessible a portion of the guidewire extending from the distal end of the catheter before the proximal end of the guidewire is disposed distal to the window element;
 an inflatable balloon member disposed on the distal end of the catheter and in communication with the inflation lumen; and
 a sleeve member slidably disposed over the catheter shaft for selectively opening and closing said window element.

9. A catheter for insertion into a patient over an elongated guidewire having proximal and distal ends, comprising:
 an elongated catheter shaft having open proximal and distal ends and a longitudinal guidewire lumen for receiving the guidewire and extending substantially the entire length of the catheter between the open ends of the catheter shaft, the catheter shaft having a length relative to the guidewire such that the guidewire receivable in said lumen can extend out the proximal and distal ends of the catheter, said catheter shaft further including a window element opening the guidewire lumen to the exterior of the catheter wherein the window element defines a shaft portion of reduced diameter, the window element having a proximal end and a distal end, the window element being located on the catheter shaft and having a length such that after the catheter has been inserted into the patient, the catheter can be withdrawn proximally over the guidewire and the window can be exposed so as to provide access to the guidewire therethrough before the proximal end of the guidewire is disposed distal to the proximal end of the catheter and such that said catheter can also be withdrawn proximally over the guidewire so that the distal end of the catheter is disposed outside of the patient so as to expose and render accessible a portion of the guidewire extending from the distal end of the catheter before the proximal end of the guidewire is disposed distal to the window element; and a wire support member wound around the reduced diameter portion of the shaft.

10. A catheter for insertion into a patient over an elongated guidewire having proximal and distal ends, comprising:

an elongated catheter shaft having open proximal and distal ends, a longitudinal inflation lumen extending the entire length of the catheter between the open ends of the catheter shaft, a longitudinal guidewire lumen for receiving the guidewire and extending substantially the entire length of the catheter between the open ends of the catheter shaft and the inflation lumen and guidewire lumen being disposed in side-by-side relationship to one another, the catheter shaft having a length relative to the guidewire such that the guidewire receivable in said lumen can extend out the proximal and distal ends of the catheter, said catheter shaft further including a window element opening the guidewire lumen to the exterior of the catheter, the window element having a proximal end and a distal end, the window element being located on the catheter shaft and having a length such that after the catheter has been inserted into the patient, the catheter can be withdrawn proximally over the guidewire and the window can be exposed so as to provide access to the guidewire therethrough before the proximal end of the guidewire is disposed distal to the proximal end of the catheter and such that said catheter can also be withdrawn proximally over the guidewire so that the distal end of the catheter is disposed outside of the patient so as to expose and render accessible a portion of the guidewire extending from the distal end of the catheter before the proximal end of the guidewire is disposed distal to the window element;

an inflatable balloon member disposed on the distal end of the catheter and in communication with the inflation lumen;

a sleeve member slidably disposed over the catheter shaft for selectively opening and closing said window element; and a first stop disposed proximal to the window and a second stop disposed distal to the window for engaging and locating said sleeve.

* * * * *